(12) United States Patent
Olsen et al.

(10) Patent No.: US 7,931,643 B2
(45) Date of Patent: Apr. 26, 2011

(54) MINIATURE PUMP FOR DRUG DELIVERY

(75) Inventors: James M. Olsen, Plymouth, MN (US); Mark S. Lent, Brooklyn Park, MN (US); James G. Skakoon, St. Paul, MN (US); Richard T. Stone, Minneapolis, MN (US); Laetitia Mayor, Fully (CH); Dale F. Seeley, Spring Park, MN (US); Michael T. Hegland, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 479 days.

(21) Appl. No.: 11/490,876

(22) Filed: Jul. 21, 2006

(65) Prior Publication Data

US 2007/0043335 A1    Feb. 22, 2007

Related U.S. Application Data

(60) Provisional application No. 60/776,016, filed on Apr. 27, 2006, provisional application No. 60/701,605, filed on Jul. 22, 2005.

(51) Int. Cl.
 *A61K 9/22* (2006.01)
 *A61M 37/00* (2006.01)
 *A61F 5/00* (2006.01)

(52) U.S. Cl. ............ 604/890.1; 604/131; 604/132; 600/40

(58) Field of Classification Search .......... 604/110, 604/263, 164.08, 192; 128/919
See application file for complete search history.

(56) References Cited

U.S. PATENT DOCUMENTS

| | | | | |
|---|---|---|---|---|
| 5,045,064 | A * | 9/1991 | Idriss | 604/132 |
| 5,306,257 | A * | 4/1994 | Zdeb | 604/131 |
| 5,312,372 | A * | 5/1994 | DeHarde et al. | 604/198 |
| 5,348,539 | A | 9/1994 | Herskowitz | |
| 5,704,520 | A * | 1/1998 | Gross | 222/334 |
| 5,814,019 | A * | 9/1998 | Steinbach et al. | 604/131 |
| 6,471,675 | B1 * | 10/2002 | Rogers et al. | 604/151 |
| 6,679,832 | B1 * | 1/2004 | Sultan | 600/40 |
| 7,108,686 | B2 * | 9/2006 | Burke et al. | 604/891.1 |
| 2004/0168723 | A1 | 9/2004 | Black | |
| 2004/0249363 | A1 * | 12/2004 | Burke et al. | 604/890.1 |
| 2006/0196552 | A1 * | 9/2006 | Kriesel et al. | 137/487.5 |

FOREIGN PATENT DOCUMENTS

EP  0 398 583 B1  4/1994
WO  WO 01/66173 A1  9/2001

* cited by examiner

*Primary Examiner* — Nicholas D Lucchesi
*Assistant Examiner* — Ian K Holloway
(74) *Attorney, Agent, or Firm* — Scott A. Marks; IPLM Group, P.A.

(57) ABSTRACT

A miniature drug delivery pump utilizes a shape memory Ni—Ti alloy. A flow restrictor is provided and the pump is refillable.

22 Claims, 18 Drawing Sheets

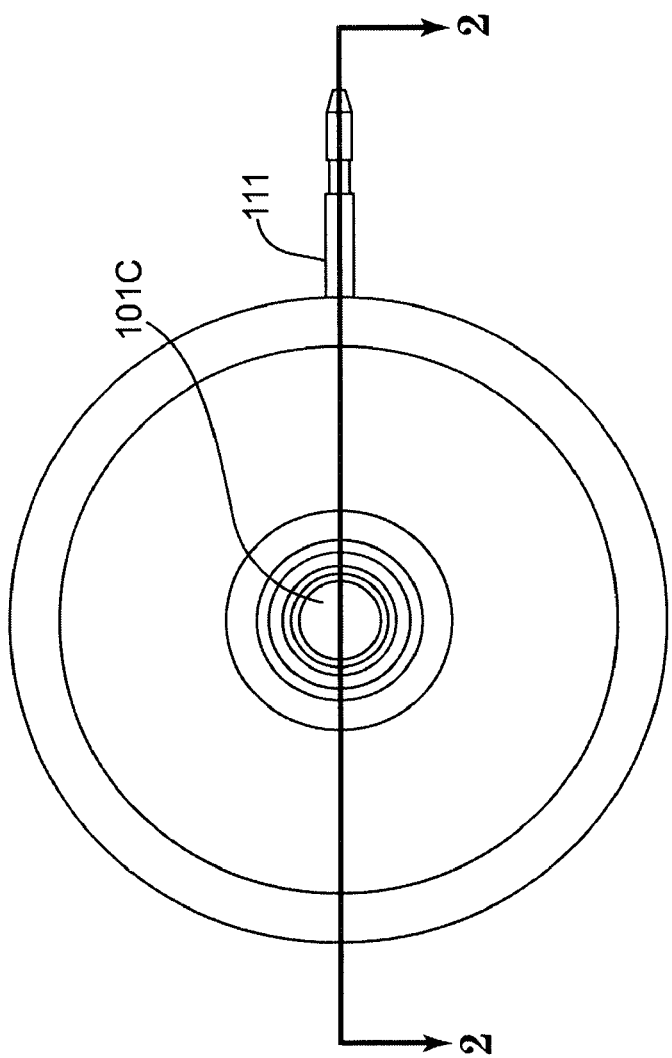
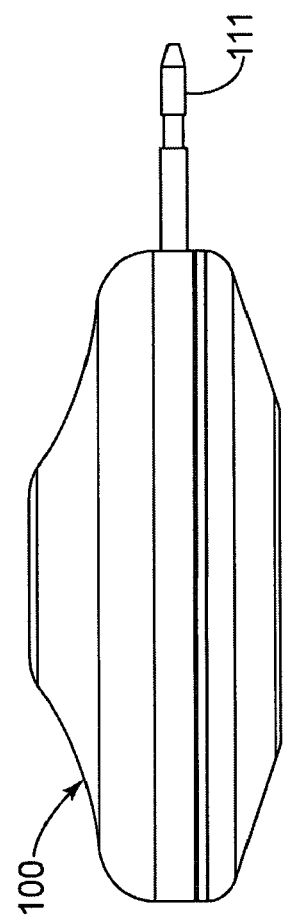
Fig. 1C
Fig. 1B

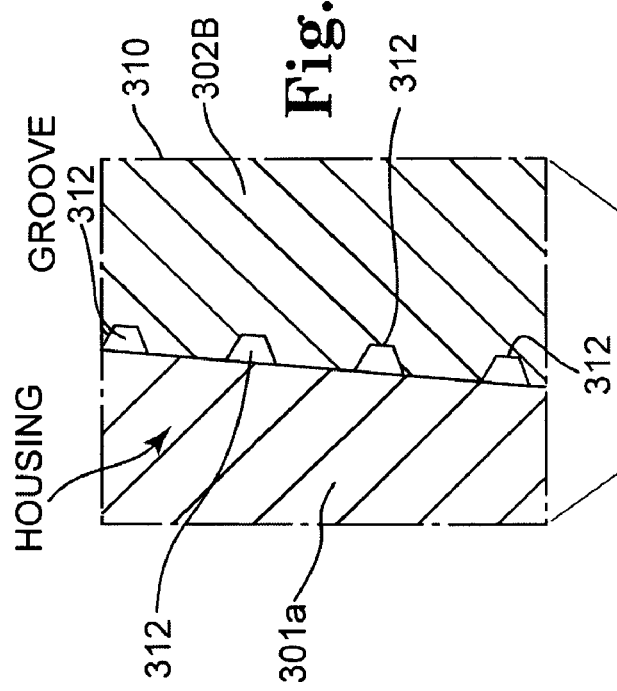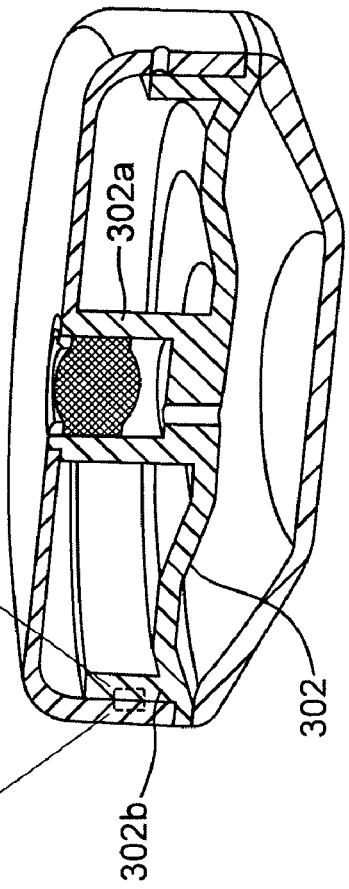

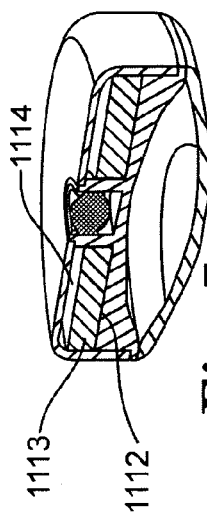
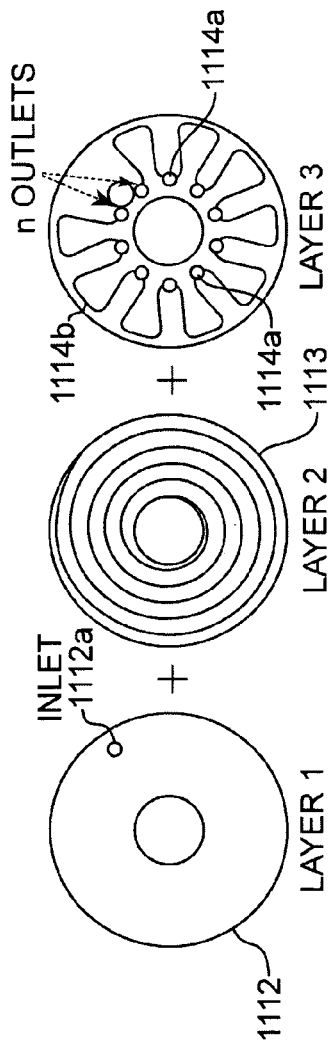
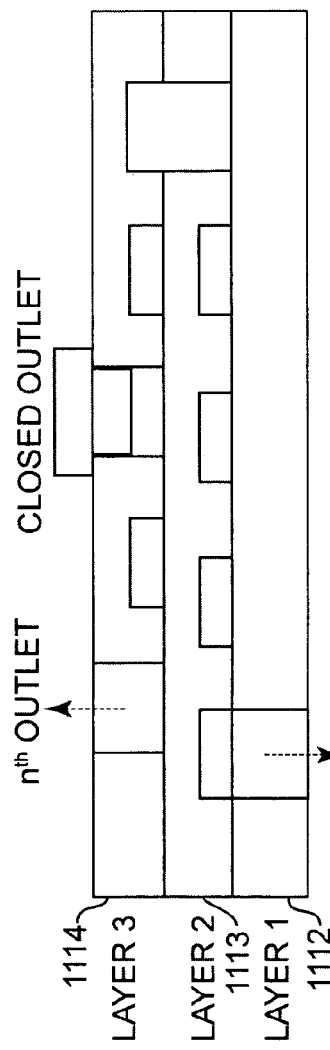
Fig. 7
Fig. 8 Layer 1
Fig. 9 Layer 2
Fig. 10 Layer 3
Fig. 11

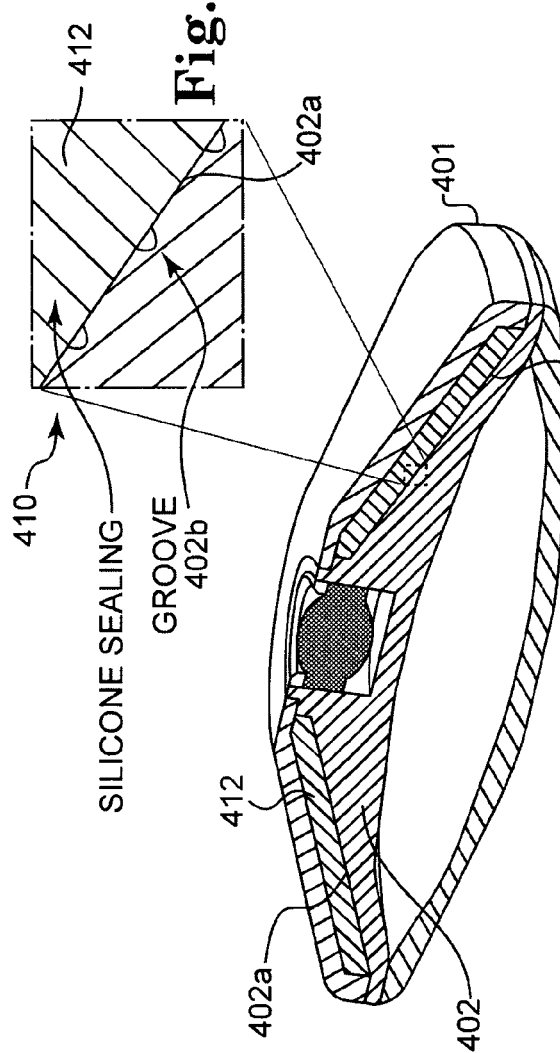
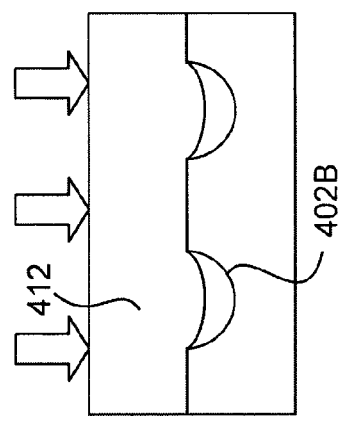
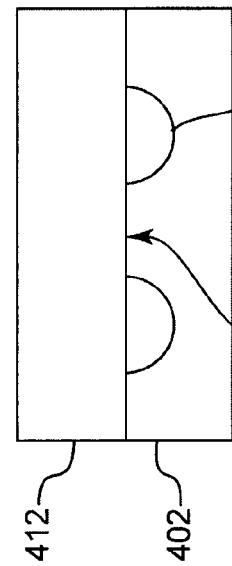
Fig. 12b
Fig. 12a
Fig. 14
Fig. 13

① OUTER DAM

② FLAT SPIRAL

③ CONICAL SPIRAL

④ PARTIAL FLAT

⑤ IN PART

⑥ NO CENTRAL SYMETRY

⑦ FOLDED GROOVE

THIN Ti SHEET

⑧ CAPILLARY (6O750)

⑨ SPIRAL FOLDED

THIN Ti SHEET

② DIFFUSION BONDING

③ SILICONE COMPRESSED 2.2.2 GROOVE CLOSING/SEALING
① HEAT STUCK IN PLACE

④ HARD COMPRESSED

⑤ MIDDLE COMPRESSION
(POLYMER)

① EDM

② PHOTOLITHOGRAPHY
(CHEMICAL ETCHING)

③ (D) - RIE

④ (WATERJET GUIDED) LASER

⑤ LIGA

⑥ MICRO - LASER SINTERING

⑦ CAPILLARY TUBE

⑨ ETCH Ti THIN LAYER
ON GLASS SUBSTRACT

① CUT AT RIGHT LENGTH

② MULTI - OUTLETS

③ VARY SECTION

④ HYBRID SYSTEM
FIXED LENGTH CAPILLARY TUBE

⑤ VARY SECTION LOCALLY

VARY LENGTH

⑥ CHOOSE BEST OUTLET

⑦ REDUCED LENGTH OF CHAMBER (AUGMENT)

X = OCCLUDED CHANNEL

① O-RING
2.2.5 CONNECTION INLET/OUTLET

② WELDED

③ DIFFUSION BONDING

④ SCREWED THREAD

② PRESSED FRIT 2.2.6 INTEGRATED FILTER
① LASER WELDED FRIT

MINIATURE PUMP FOR DRUG DELIVERY

This application claims priority to U.S. Patent Application 60/776,016, filed Apr. 27, 2006 and U.S. Patent Application 60/701,605, filed Jul. 22, 2005, these applications being incorporated by reference herein.

FIELD OF THE INVENTION

The present invention relates to a miniature infusion device or pump for the delivery of drugs, and more particularly to a pump utilizing a reservoir having a shape memory alloy that is either superelastic or superdeformable diaphragm.

BACKGROUND OF THE INVENTION

Fixed rate drug delivery pumps have typically utilized a metal bellows reservoir with a two-phase propellant to keep the drug at a constant pressure of approximately 36 p.s.i. The drug flows out of the reservoir through a flow restrictor, such as a glass capillary tube that has been calibrated to produce the desired flow rate. Fixed rate pumps are typically 80 cc to 100 cc in size. The reservoir utilizes a metal bellows that is made out of suitable metal such as titanium. However, such metal bellows typically are not very elastic and the reservoir needs to be relatively large in size to accommodate the accordion leaves. Such a construction has prevented the design of a smaller pump and is expensive. The present invention addresses the problems associated with the prior art pumps and may be utilized in either a fixed rate or a variable rate smaller sized pump for the delivery of drugs.

SUMMARY OF THE INVENTION

In one embodiment, the invention is an infusion device for use in delivering drugs. The infusion device includes a housing having a chamber. The housing has an outlet. The diaphragm is operatively connected to the pump housing, the diaphragm dividing the chamber into a drug storage subchamber and a propellant subchamber, the diaphragm configured to go over center for greater volume efficiencies. The propellant subchamber is adapted and configured to receive a suitable propellant. The drug subchamber is adapted and configured to receive a suitable drug, the drug storage subchamber having an outlet in fluid communication with the outlet of the housing.

In another embodiment, the invention is an infusion device for use in delivering drugs. The infusion device includes a housing having a chamber, the housing having an outlet. A diaphragm is operatively connected to the housing, the diaphragm dividing the chamber into a drug storage subchamber and a propellant subchamber, the diaphragm constructed from a shape memory alloy material. The propellant chamber is adapted and configured to receive a suitable propellant and the drug storage subchamber is adapted and configured to receive a suitable drug, the drug storage subchamber having an outlet in fluid communication with the outlet of the housing.

In another embodiment, the invention is an infusion device for use in delivering drugs. The infusion device includes a housing having a chamber, the housing having an outlet. A diaphragm is operatively connected to the housing, the diaphragm dividing the chamber into a drug storage subchamber and a propellant subchamber. The diaphragm is constructed from a shape memory alloy. The propellant subchamber is adapted and configured to receive a suitable propellant. The drug storage subchamber is adapted and configured to receive a suitable drug, the drug storage subchamber having an outlet in fluid communication with the outlet of the housing. A flow restrictor has a first end in fluid communication with the outlet of the drug storage subchamber and a second end in fluid communication with the housing outlet. The flow restrictor being a micro-machine flow restrictor, the flow restrictor includes a first glass member having a top planar surface. A second glass member has a planar bottom surface, the bottom surface of the second glass member positioned on the top surface of the first glass member to form a chip assembly. One of the top surface and bottom surface having a channel machined thereon. The chip assembly has an inlet in fluid communication with the drug storage subchamber outlet and an outlet in fluid communication with the housing outlet.

BRIEF DESCRIPTION OF THE DRAWINGS

FIG. 1b is a side elevational view of the pump of FIG. 1;

FIG. 1c is a top plan view of the pump of FIG. 1;

FIG. 6a is a perspective view of another embodiment of a pump according to the present invention with portions broken away;

FIG. 6b is an enlarged view of a portion of the pump shown in FIG. 6a;

FIG. 7 is a perspective view, with portions broken away, of another embodiment of a pump according to the present invention;

FIG. 8 is a top plan view a first layer of a flow restrictor shown in FIG. 7;

FIG. 9 is a top plan view of a second layer of a flow restrictor shown in FIG. 7;

FIG. 10 is a top plan view of a third layer of a flow restrictor shown in FIG. 7;

FIG. 11 is an enlarged side elevational view of the layers shown in FIGS. 8-10, assembled;

FIG. 12a is a perspective view, with portions broken away, of another embodiment of a pump according to the present invention;

FIG. 12b is an enlarged view of a portion of the pump shown in FIG. 12a;

FIG. 13 and FIG. 14 are two views showing the process for making the flow restrictor shown in FIG. 12b;

DETAILED DESCRIPTION OF THE INVENTION

Figure 1A:
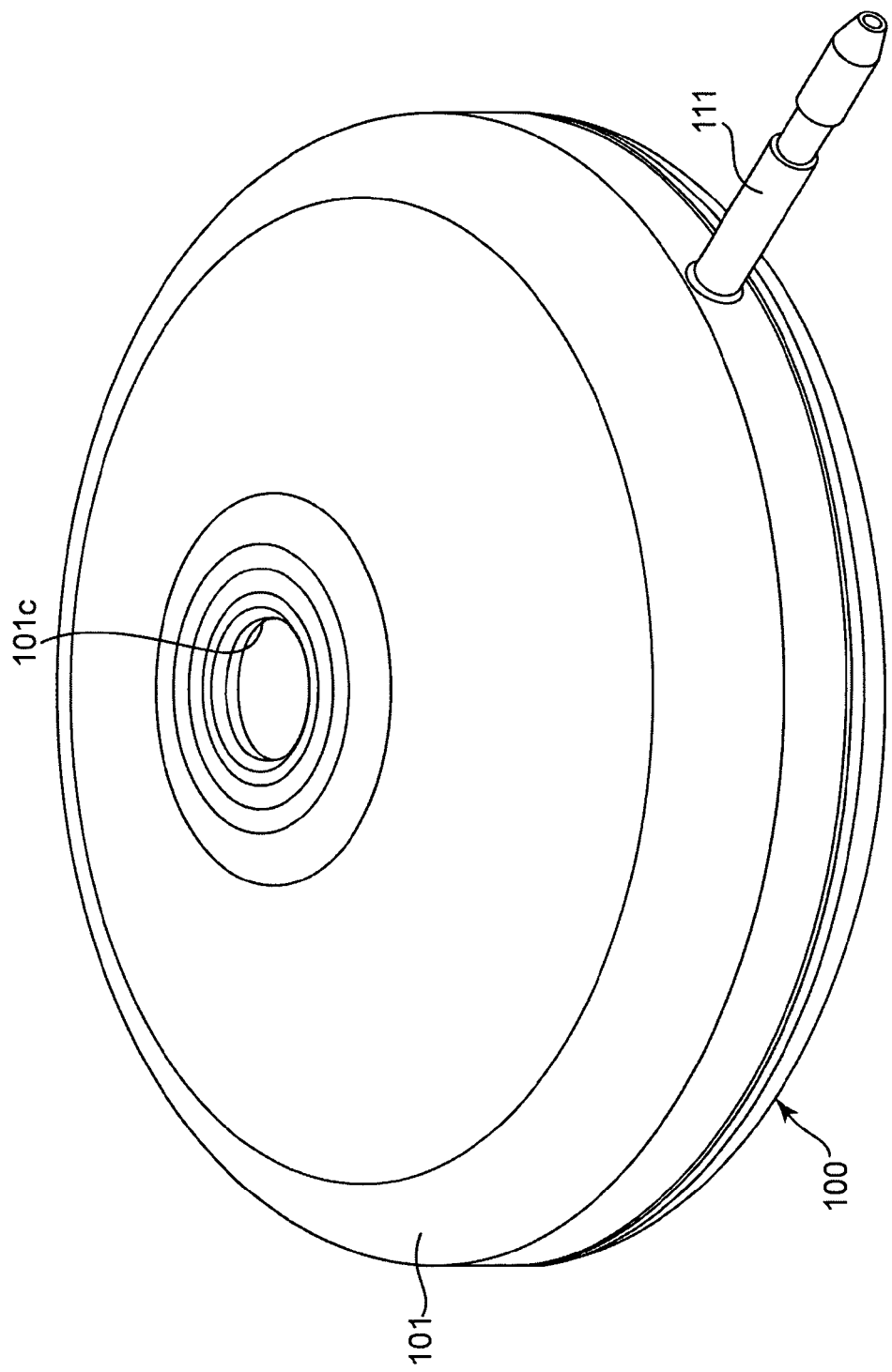
FIG 1a shows a perspective view of a first embodiment of a pump according to the present invention.
Figure 2:
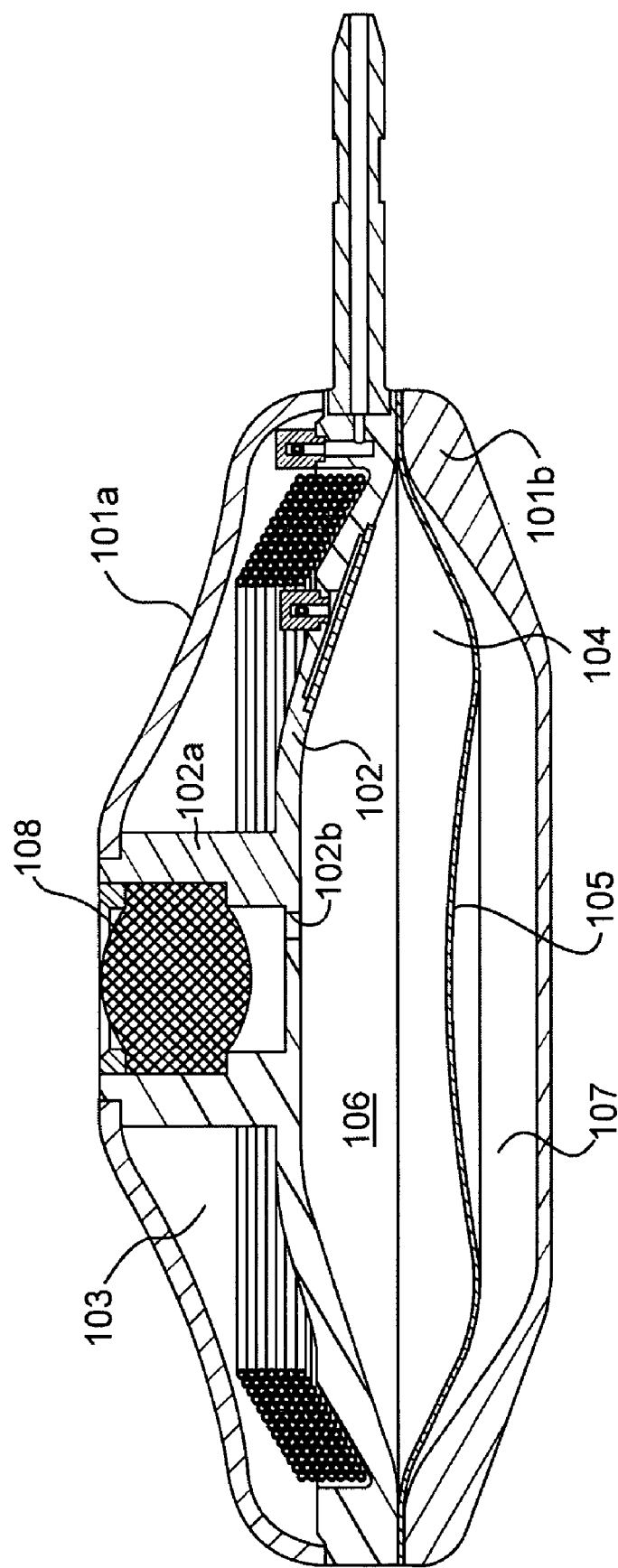
FIG. 2 is a cross-sectional view of the pump shown in FIG. 1c taken generally along the lines 2-2.
Figure 3:
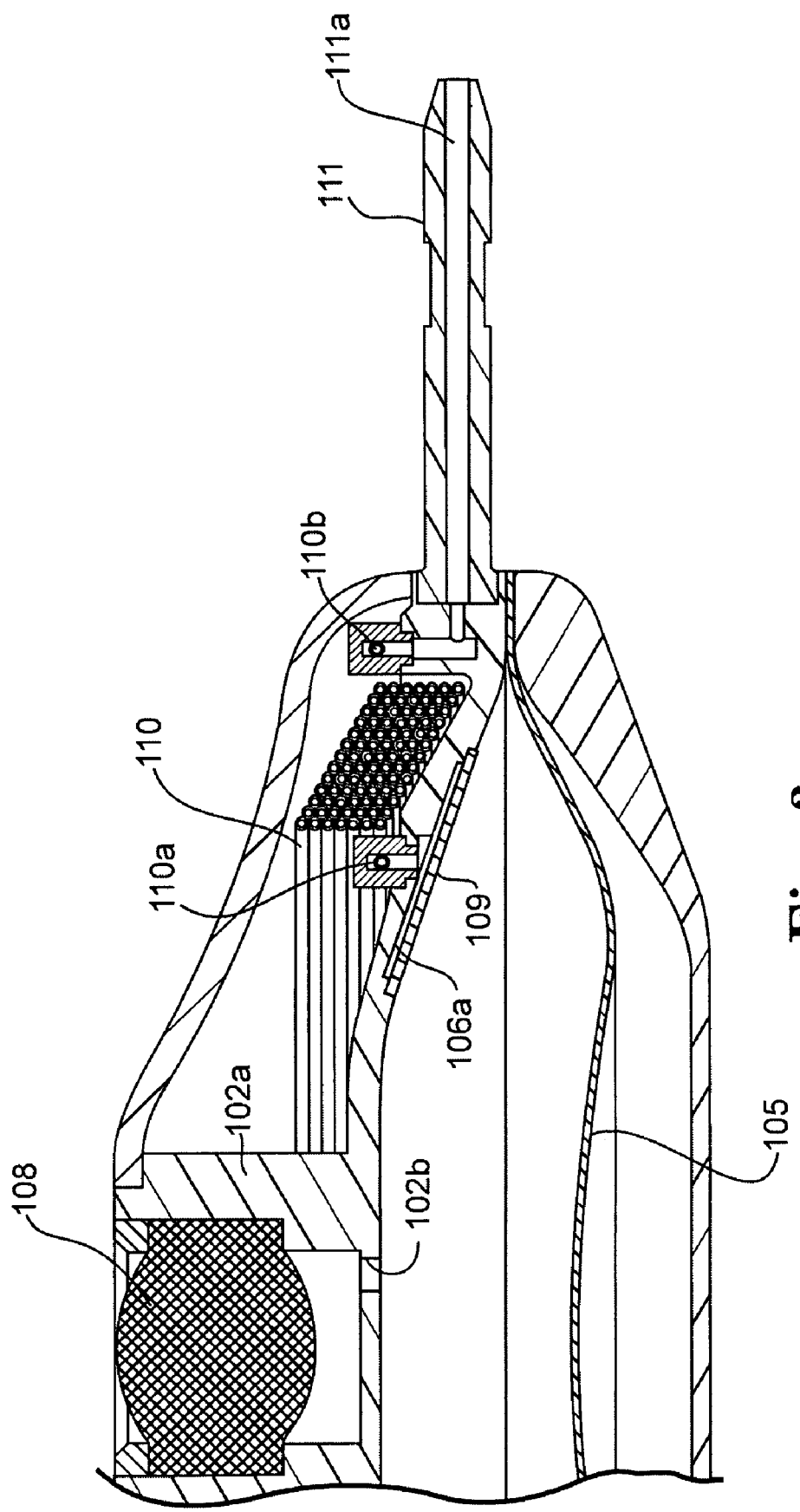
FIG. 3 is an enlarged view of a portion of FIG. 2.

Referring to the drawings, where in-like numerals represent like parts throughout the several views, there is generally disclosed at 100 a miniature pump for the delivery of drugs. While it is understood the pump 100 and other embodiments of pumps to be described hereinafter may be described as implantable, it is understood that the pumps may also be used as pumps that are not implantable, such as patch pumps. Referring now to FIGS. 1*a* through 1*c*, FIG. 2 and FIG. 3, the pump 100 includes a suitable housing 101 having a top half 101*a* and a bottom half 101*b*. An interior wall 102 is operatively connected to the housing and divides the interior of the housing 101 into an upper cavity 103 and lower cavity 104. A dome shaped diaphragm 105 is operatively connected to the housing 101 and interior wall 102 and divides the lower cavity 104 into a drug storage subchamber 106 and a propellant subchamber 107. The propellant subchamber 107 may be filled with any suitable propellant such as a two-phase propellant, as is well known in the art. The diaphragm 105 is made from a shape memory alloy metal such as NITINOL, a superelastic or superdeformable Ni—Ti alloy. The superelastic metal materials allow for a thin membrane to be displaced many cycles while encountering large strain and not fracture. By being superelastic, it is able to undergo large elastic deformation or strain when compared to typical metals. The thin round diaphragm 105 has a dome shape that will allow movement of the membrane as the drug storage subchamber 106 changes from full to empty. The primary resulting bending stresses of the diaphragm 105 are low and do not impart significant pressure changes to the drug in the drug storage subchamber 106. The diaphragm 105 may be constructed out of a superelastic type of material such as Ni—Ti alloy, Nitinol. While the specific make-up of NITINOL may vary depending on the characteristics required, NITINOL is approximately 55% Ni and 45% Ti, or viewed another way, the Ni and Ti are approximately 50 atomic percent each. Using this material in either its Austenitic phase or Martensitic phase can produce useful results. The Nitinol material can be designated to tolerate the large strains induced by the diaphragm 105 bending during the drug reservoir changing from full to empty. The Austenitic phase material provides superelastic properties to accommodate the bending without any permanent deformation and no permanent strain after unloading (cycling from full to empty). The Martensitic phase material provides superdeformable properties the ability to undergo large strains and deformation without fracture and further provides an advantage of its relative softness that reduces pressure changes on the drug held in the drug storage subchamber 106. Other materials such as Titanium or Tantalum have good biocompatibility and drug compatibility and can accommodate high strain conditions adequately before fatigue characteristics initiate cracks. While it is preferred to use the superelastic material, Titanium or Tantalum may also be useful in certain circumstances. The Titanium and Tantalum may not be able to endure the large number of cycles that would be available with a superelastic material. However, in such instances, the diaphragm, made out of Titanium or Tantalum may still be applicable for applications requiring fewer cycles. In addition, the Titanium or Tantalum diaphragm 105 may be more compatible with the specific composition of the drug.

The interior wall 102 has an inlet portion 102*a* in which a septum 108 is positioned. The housing 101 has an opening 101*c* to allow access, through the septum 108, to the drug storage subchamber 106. The inlet portion 102*a* has a bore 102*b* that provides for fluid communication into the drug storage subchamber 106. A suitable type filter, such as a titanium filter 109 is positioned approximate to the outlet 106*a* of the subchamber 106. This filters the drug as it exits the subchamber 106 and enters the flow restrictor 110. The flow restrictor 110 shown in the figures is a circular capillary tube having an inlet 110*a* and an outlet 110*b*. The inlet 110*a* and outlet 110*b* may be placed in fluid communication by means well known in the art and by means to each described hereafter. The outlet 110*b* is in fluid communication with the pump outlet 111 which has a bore 111*a* through which the drug passes out of the pump 100.

As shown in FIGS. 1*a*-1*c*, 2 and 3, the pump 100 has a height of approximately 9 mm and a diameter of approximately 27 mm and an overall size of approximately 4 cubic centimeters (cc). This has a drug storage subchamber 106 of approximately 1 ml. It is recognized that the pump 100 could be larger, approximately 30 cc, with a corresponding increase in subchamber 106 to 10 ml which is still considered a small pump.

Figure 4:
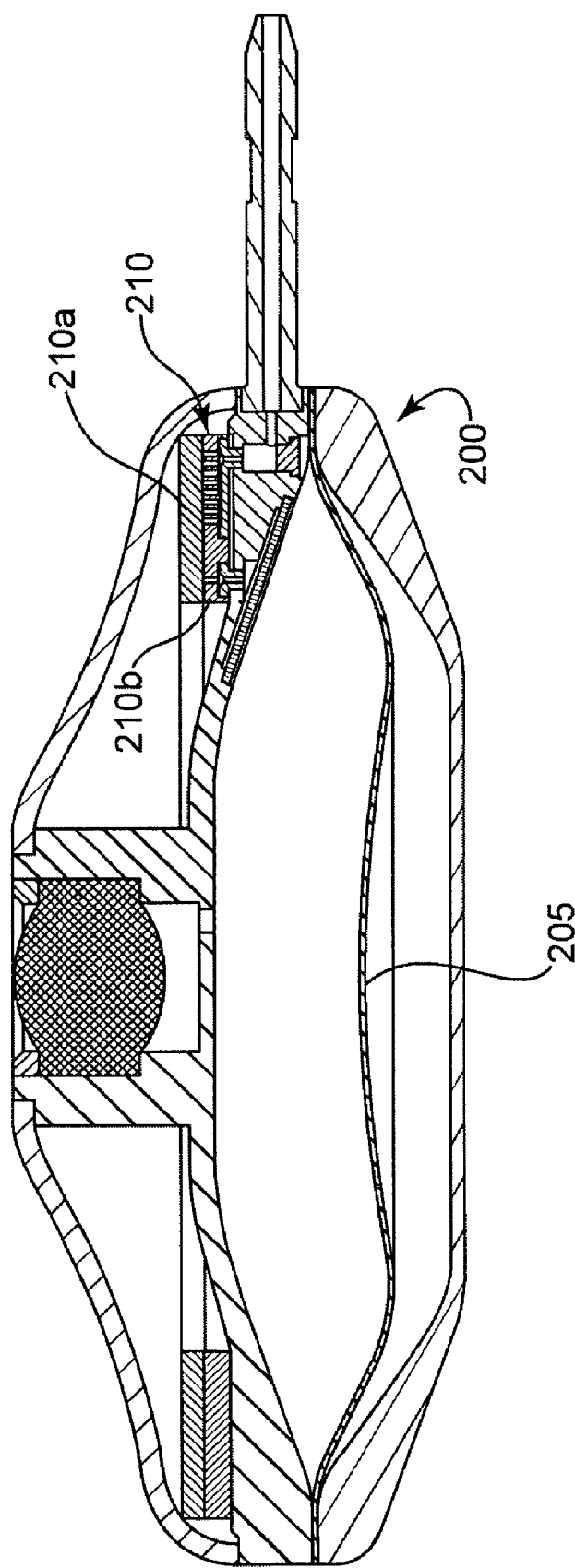
FIG. 4 is a cross-sectional view of another embodiment of a pump according to the present invention.
Figure 5:
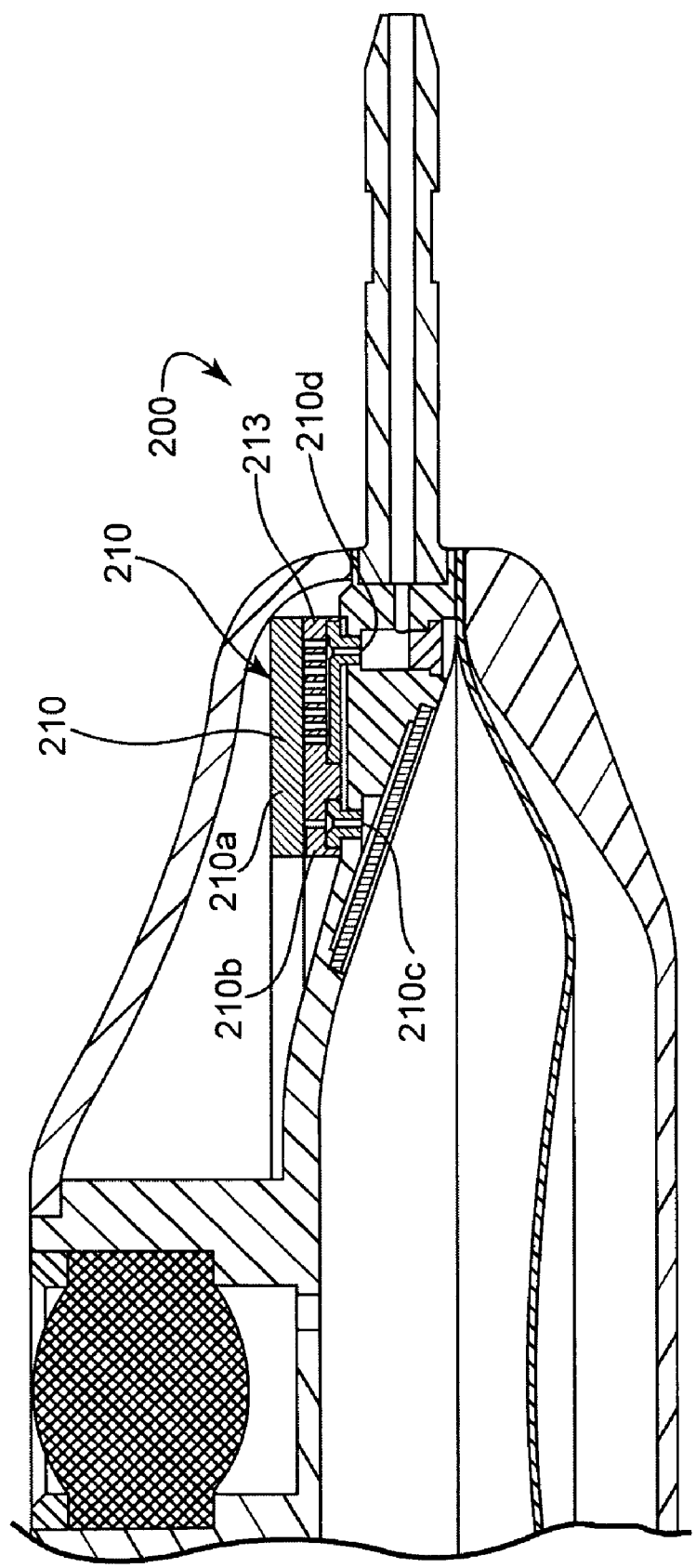
FIG. 5 is an enlarged view of a portion of FIG. 4.

Referring now to FIGS. 4 and 5, there is shown a second embodiment of a pump 200. The pump 200 is similar to pump 100 with the use of a different flow restrictor. Accordingly, only the flow restrictor 210 will be described in detail, it being recognized that the other components, such as diaphragm 205 are similar. The flow restrictor 210 includes a first cover layer 210*a*. A second layer 210*b* includes fixed restriction passages as well as variable or adjustable passageways and finally the inlet 210*c* are all contained in this layer 210*b*. The material for such a flow restrictor 210 may be pyrex or flowd glass or titanium. These layers are in a flat doughnut shape.

FIGS. 6*a* and 6*b* show another embodiment of a pump 300. The pump 300 is being shown to describe in more detail a flow restrictor 310. The drawings do not show some of the component parts of the pump 300 such as a diaphragm and some of the other components. However, one skilled in the art would understand how such a pump would be constructed. The pump 300, as previously mentioned, shows the interior wall 302 having an inlet portion 302*a* and an outer ring 302*b*. The flow restrictor 310 is formed by forming a plurality of grooves 312 in the outer ring 302*b*. The grooves are formed in a continuous spiral. The materials for the interior wall 302 and housing 301 may be made of a suitable material such as titanium. Suitable dimensions for the grooves would be a width of approximately 50 microns, a depth of 15 microns and a pitch of 100 microns. However, it is understood that other suitable dimensions may be utilized for the groove, depending upon the flow rate desired. The two parts, the housing 301 and the outer ring 302*b*, may be suitably connected by means such as heat shrinking, as will be discussed more fully hereafter.

Referring now to FIGS. 7 through 11, there is shown another embodiment of a pump 1100. The pump 1100 is similar to pump 200 with the use of a different flow restrictor. Accordingly, only the flow restrictor 1110 will be described in detail, it being recognized that the other components, such as diaphragm (not shown) are similar. The pump 1100 is also shown in less detail, in FIG. 7, with the portions of the flow restrictor 1110 showing more detail in FIGS. 8-11. The flow restrictor 1110 includes a first layer 1112 having an inlet 1112a On top of the first layer is second layer 1113 on which there is a spiral flow path 1113a. A third layer 1114 is positioned on top and has a plurality of outlets 1114a along with a flow path 1114b. The third layer may be rotated so that a particular outlet 1114a is used. This will vary the length of the flow path 1114b and therefore create different flow rates. The material for such a flow restrictor 1110 may be pyrex or flowd glass or titanium. Possible dimensions of the layers 1112-1114 are an outer diameter of 25 mm, an inner diameter of 6 mm and a thickness of approximately 1.5 mm.

Referring now to FIGS. 12a, 12b, FIG. 13 and FIG. 14, there is shown another embodiment of a pump 400. Again, the pump 400 is being shown to describe a suitable flow restrictor and accordingly a number of the parts in the pump, such as a diaphragm, similar to diaphragm 105, are not shown. The interior wall 402 has a top surface 402a into which a plurality of grooves 402b are formed. While the interior wall 402 and housing 401 are formed of a suitable material, such as titanium, a silicone seal 412 is positioned between the top surface 402a and the housing 401. The grooves 402b are again a continuous spiral and may have suitable dimensions such as a width of 30 microns and a depth of 15 microns. Chemical etching is one suitable method of making the grooves. As shown in FIGS. 13 and 14, the silicone seal 412 is placed on the interior wall 402 and heat and/or pressure is applied forcing the silicone seal 412 partially into the grooves 402b. Depending upon the force applied, the amount of silicone seal 412 that is displace into the groove 402b will vary, thereby varying the flow characteristics of the flow restrictor 410.

The flow restrictors in the pumps described thus far, are intended to provide flow rates of approximately 1 ml per month. Therefore, extremely small channels or passages are desired. To achieve this, the designs previously discussed have been utilized. A more detailed description of various designs that may be utilized in a suitable flow restrictor are shown in FIGS. 15-47 and will be described hereafter.

Generally, a groove is place on a layer of material and then covered by another layer to enclose the groove and make the required passageway. The passage may be shaped in any number of patterns to achieve the necessary length. Likewise, more than one layer of passages can be combined in the final chip assembly. This general concept can be completed by a combination of groove technology, bonding and calibration.

The groove can be etched by using wet etching methods such as photolithography and chemical etching, deep reacting ion etching (DRIE), ion etching, lithography, electroplating, injection molding (LIGA). The groove may be enclosed by bonding a layer on top of the etched layer by using methods such ionic bonding, diffusion bonding or compressing an elastomer layer on top of etched channels. The size and length of the passage are used to determine exact restriction that is desired that is used to contribute overall flow accuracy of the device. To achieve the accurate restriction, either the groove size must be controlled to precise dimensions or the length can be calibrated by one of a number of methods. These methods include high precision etching to less than 1um variation such that no calibration is required; multiple outlets near the end of the length that can be plugged by choosing the appropriate number or location of the plugged holes to provide the calibrated length; including pathways to block a loop or selected area of the passage; or varying the depth of the channel during bonding or by the amount of compression of a covering elastomer layer.

Figure 15:
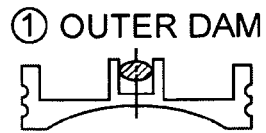
FIGS. 15-23 show various embodiments of groove placement for making flow restrictors for the pumps according to the present invention, such as the pump shown in FIG. 6.
Figure 16:
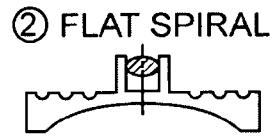
Figure 17:
Figure 18:
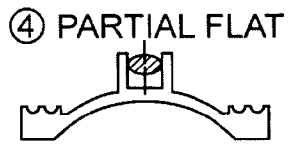
Figure 19:
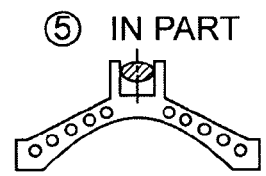
Figure 20:
Figure 21:
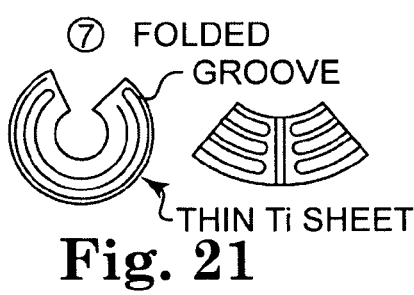
Figure 22:
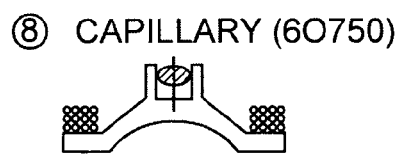

Referring to FIGS. 15-43, a number of these concepts are shown. FIG. 15 shows the grooves formed in the outer diameter of the interior wall. FIG. 16 is illustrative of a flat spiral on the outer wall. FIG. 17 illustrates a conical spiral on the interior wall. FIG. 18 discloses a partial flat groove on the interior wall. FIG. 19 discloses an in-part construction utilizing micro-laser sintering. FIG. 20 is an illustration where there is no central symmetry for the groove. FIG. 21 illustrates where a titanium sheet is constructed with a plurality of grooves and is then folded to a conical shape. FIG. 22 is an illustration of the glass capillary tube as previously shown in FIGS. 2 and 3. There, the inner diameter of the glass capillary tube may be approximately 40 microns with an outer diameter of 100 microns. The tube would be cut to the appropriate length for the proper calibration.

Figure 23:
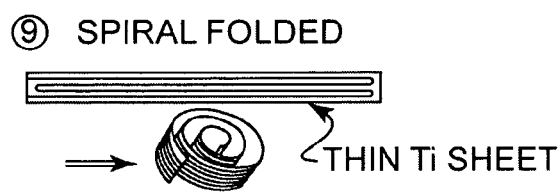

FIG. 23 illustrates a titanium sheet where a groove is formed in the flat sheet and is then spirally folded.

Figure 25:
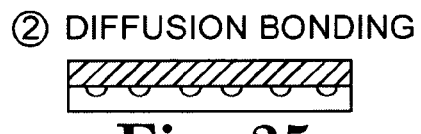
FIGS. 24-28 are embodiments showing technology for groove closing and sealing for flow restrictors for use with the present invention.
Figure 26:
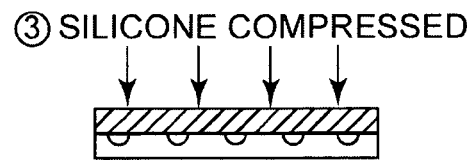
Figure 24:
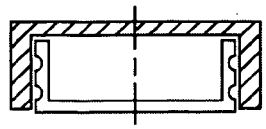
Figure 27:
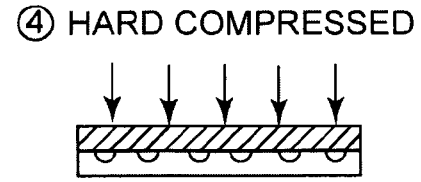
Figure 28:
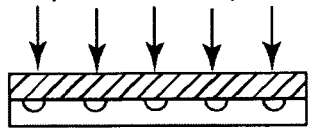

FIGS. 24 through 28 are illustrative of various groove closing or sealing techniques. FIG. 24 illustrates where the groove and covering piece are assembled with an interference fit using a heat. differential to create the interference fit. FIG. 25 is illustrative of diffusion bonding. The diffusion bonding is well known and uses heat and pressure. FIG. 26 is illustrative of compressed silicone, as shown with respect to FIGS. 13 and 14. FIG. 27 shows a hard compression and FIG. 28 shows a middle compression.

Figure 29:
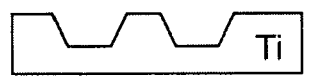
FIGS. 29-36 show embodiments for the production of grooves for making the flow restrictors for use with the present invention.
Figure 30:
Figure 31:
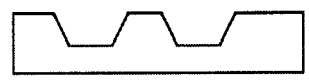
Figure 32:
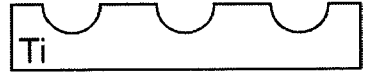
Figure 33:
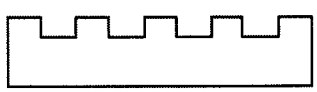
Figure 34:
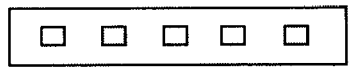
Figure 35:
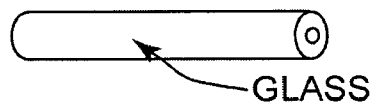
Figure 36:

FIGS. 29 through 36 illustrate various groove production technologies. FIG. 29 shows electric discharge machine (EDM) technology. FIG. 30 is illustrative of photolithography or chemical etching. FIG. 31 shows deep reactive ion etching and FIG. 32 shows water jet guided laser technology. FIG. 33 illustrates lithography electroplating injection molding (LIGA) and FIG. 34 shows micro-laser sintering. FIG. 35 shows a glass capillary tube and finally FIG. 36 shows etching a thin titanium layer on a glass substrate.

Figure 37:
FIGS. 37-43 are figures showing various flow restrictors utilizing different designs for calibration.
Figure 38:
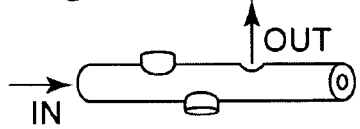
Figure 39:
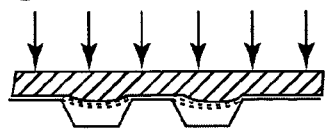
Figure 40:
Figure 41:
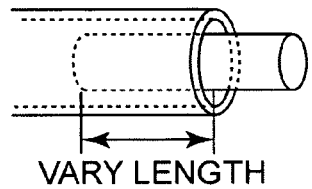
Figure 42:
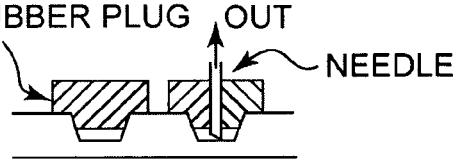
Figure 43:
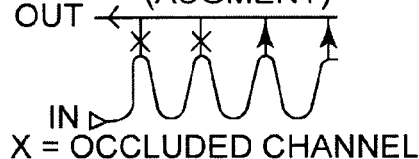

FIGS. 37-43 are illustrative of methods of calibration of a flow restrictor. FIG. 37 illustrates the cutting of a glass capillary tube to a desired length. FIG. 38 illustrates a capillary having multiple outlets and selecting the proper outlet for the correct length and plugging the other outlets. FIG. 39 illustrates the varying cross sections of the groove (represented by the dashed lines) to vary the flow rate. FIG. 40 is illustrative of a combination system with a fixed length of a capillary tube and a micro machined section for calibration or adjustment. FIG. 41 shows varying a section length locally. FIG. 42 shows selecting the correct outlet with a rubber plug and removing the other. FIG. 43 is illustrative of reducing the length of the channel by occluding those channels that are marked with an x, thus varying the length.

It is necessary to have a means to connect the flow restrictor to the inlet and outlet portions of the flow path. The connector can be diffusion bonded or compressed with o-rings or other gaskets, welded or screwed as shown in FIGS. 44-47.

Figure 44:
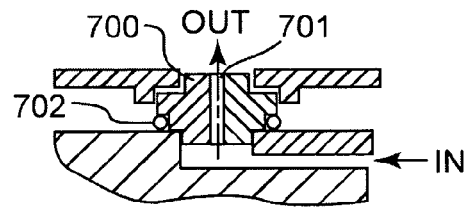
FIGS. 44-47 are embodiments of various connections for connecting the flow restrictor to inlet and outlet portions of the flow path.
Figure 45:
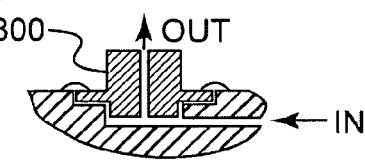
Figure 46:
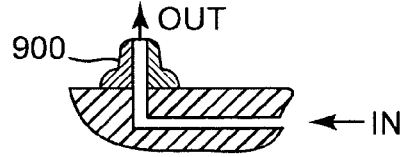
Figure 47:
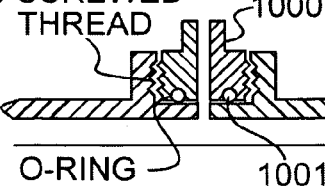

FIGS. 44-47 are illustrative of different connections of the flowpath. It is necessary to connect the groove in the flow restrictor to both the subchamber containing the drug of the pump outlet. FIG. 44 illustrates a fitment 700 that has a bore 701 through it. The fitment is sealed with an o-ring 702. FIG. 45 shows the welding of fitment 800, thereby forming a seal. FIG. 46 shows diffusion bonding of an insert 900. FIG. 47 is illustrative of a threaded fitment 1000 that is threaded to a portion approximate to the flow restrictor. An o-ring 1001 is utilized for sealing.

Figure 49:
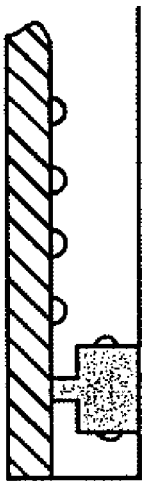
FIGS. 48-49 show two embodiments of an integrated filter for use with the pumps of the present invention.
Figure 48:
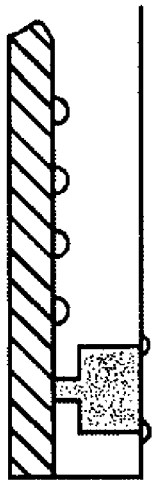

FIGS. 48 and 49 are illustrative of an integrated titanium filter being either laser welded as shown in FIG. 48 or a press fit as shown in FIG. 49.

Referring now to FIGS. 50-57, there is shown another embodiment of a pump 500. The pump 500 is showing a pump that may be used as a prototype. Accordingly, certain portions of the construction are shown that are advantageous for a prototype design, that would not necessarily be incorporated into a production design. The pump 500 includes a suitable housing 501. The housing includes a top half 501a, a bottom half 501b and an interior wall or bulkhead 502. The interior wall 502 is operatively connected to the. housing and divides the interior of the housing 501 into an upper cavity 503 and a lower cavity 504. A diaphragm 505 is operatively connected to the housing and the interior wall 502 and the diaphragm 505 divides the lower cavity 504 into a drug storage subchamber 506 and a propellant chamber 507. Again, the diaphragm 505 is a superelastic material such as Nitinol. While not shown in FIG. 51, the diaphragm 505 may take the same shape as the diaphragm 105 shown in FIGS. 2 and 3. The propellant chamber 507 may be filled by any suitable propellant such as two-phase propellant, as is well known in the art. A propellant passageway 540 is formed in the bottom half 501b and is in fluid communication with the propellant chamber 507. A gas pin 541 is insertable in the propellant passageway 540 to contain the propellant in the propellant subchamber 507, after being filled.

The interior wall 502 has an inlet portion 502a in which a septum 508 is positioned. A septum ring 542 may be utilized and the septum 508 may be positioned therein. The housing 501 has an opening 501c to allow access, through the septum 508, to the drug storage subchamber 506. The inlet portion 502a has a bore 502b that provides for fluid communication into the drug storage subchamber 506. A suitable type filter, such as a Titanium filter 509 is positioned approximate to the outlet 506a of the subchamber 506. This filters the drug as it exits the subchamber 506 and enters a flow restrictor 510. The components, thus far described for pump 500, may be assembled by means well known in the art, and may include welding.

Figure 50:
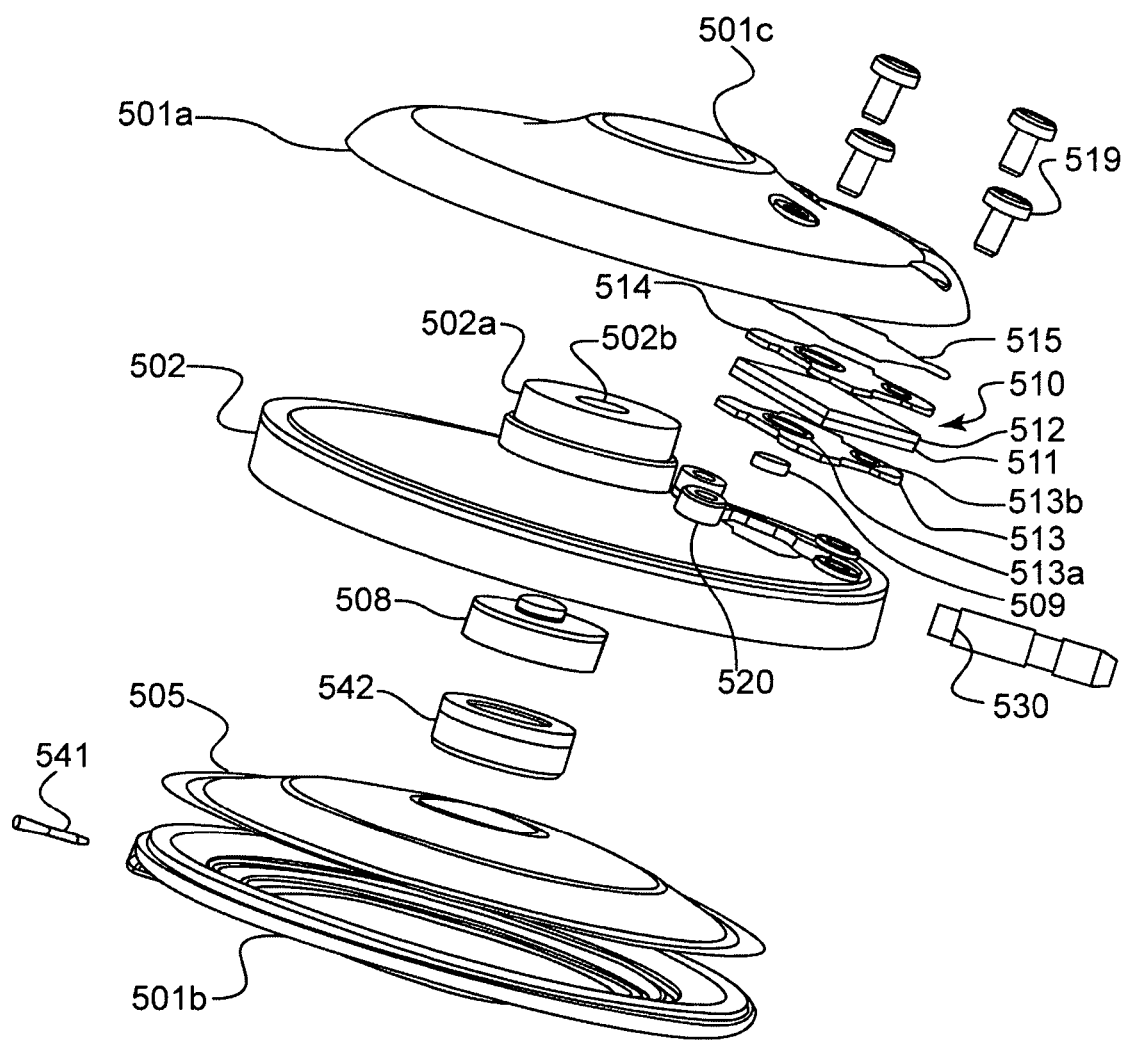
FIG. 50 is an exploded perspective view of another embodiment of the present invention.
Figure 51:
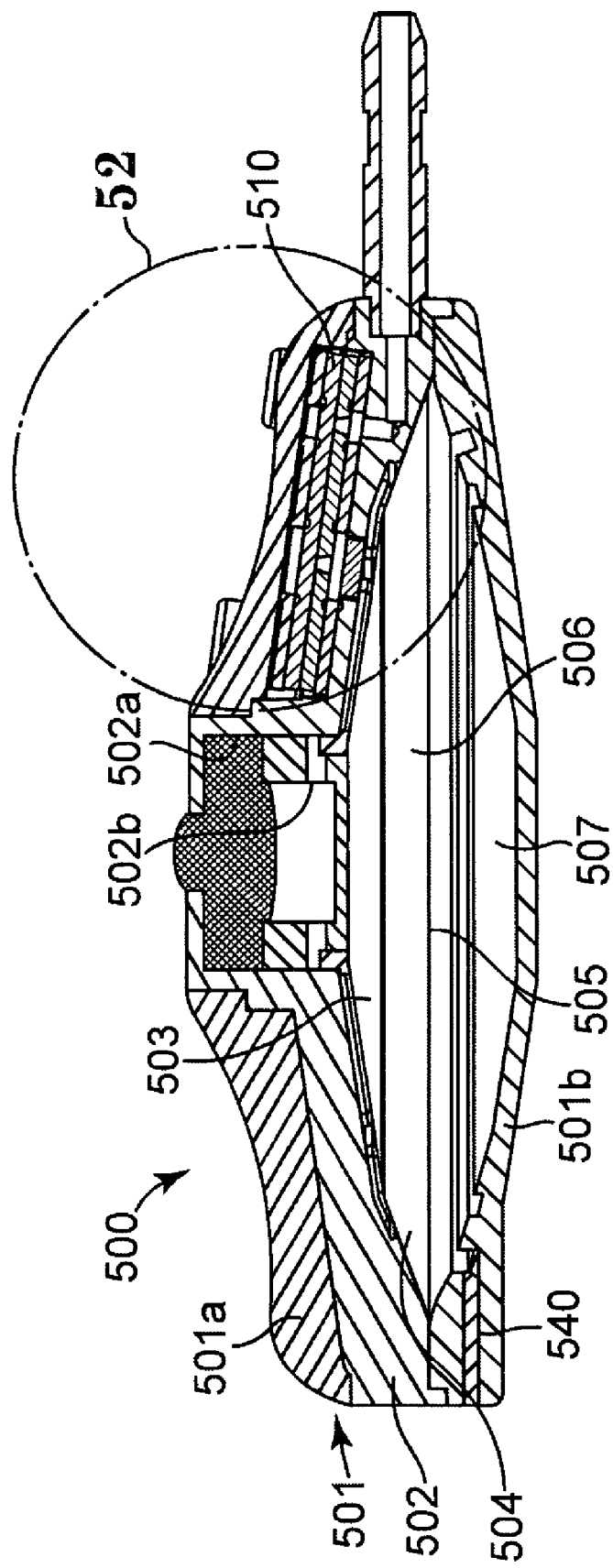
FIG. 51 is a cross-sectional view of the embodiment shown in FIG. 50.
Figure 52:
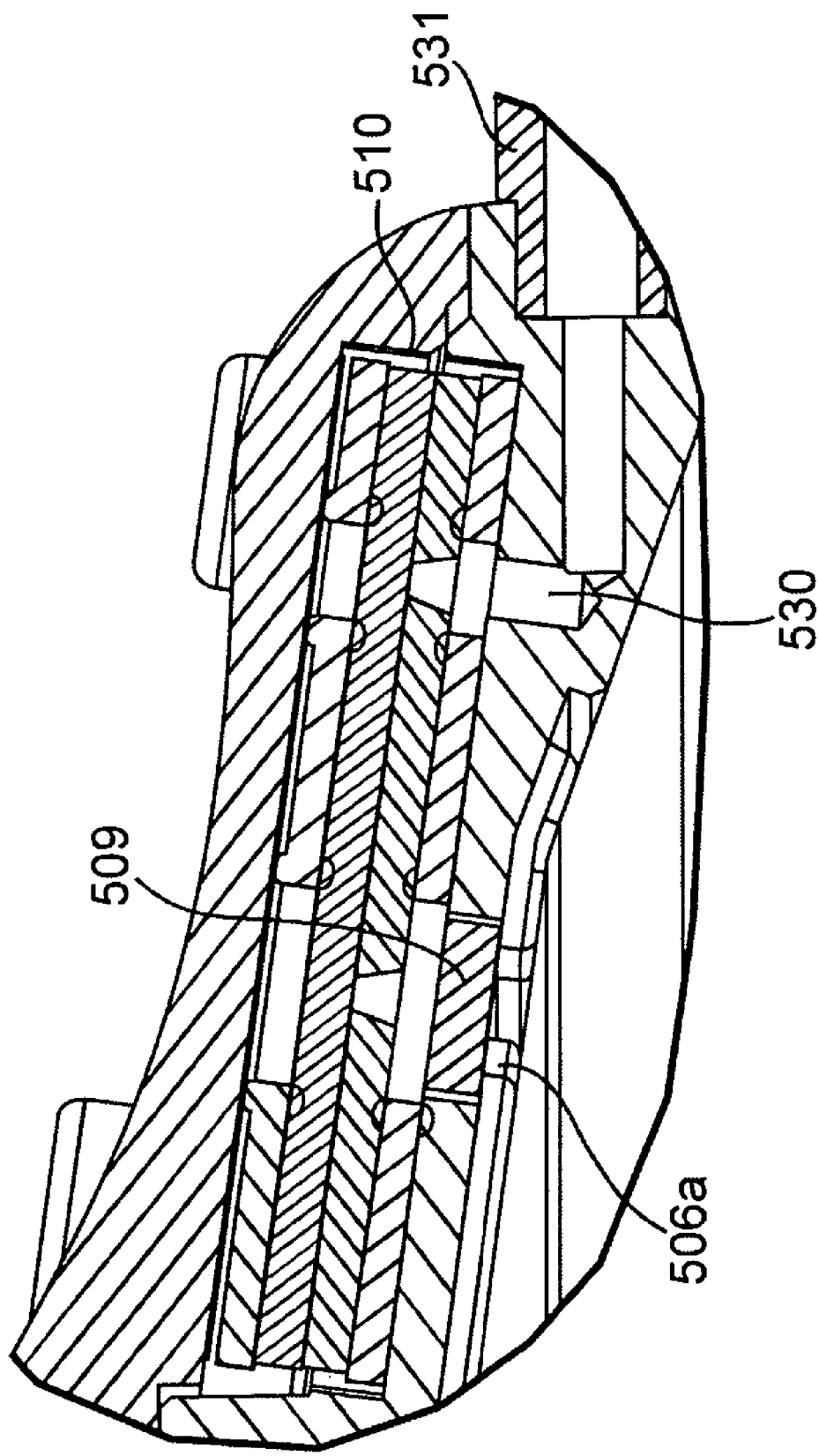
FIG. 52 is an enlarged cross-sectional view of the portion shown in FIG. 51.
Figure 55:
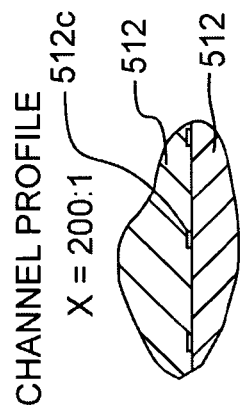
FIG. 55 is an enlarged cross-sectional view of a portion, labeled X, in FIG. 54.
Figure 53:
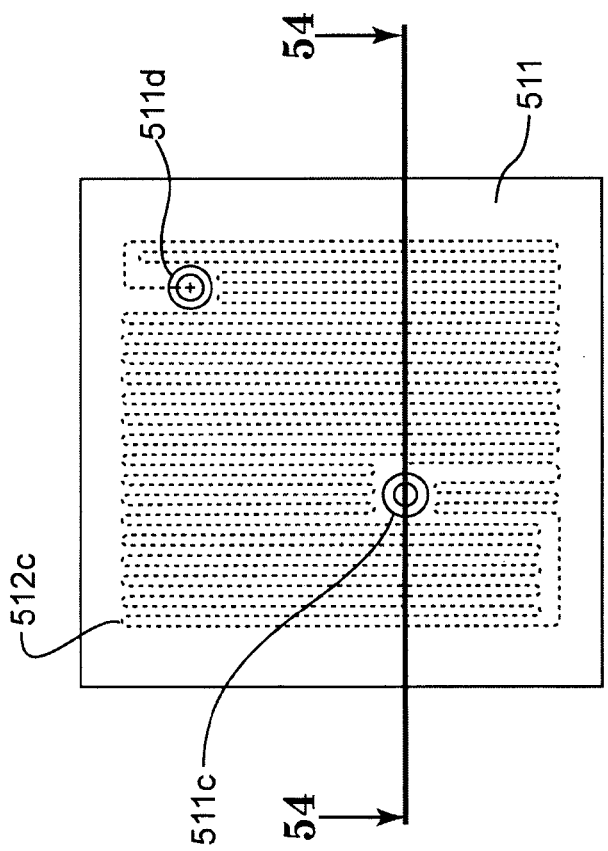
FIG. 53 is a top plan view of the chip assembly shown in FIG. 50.
Figure 54:
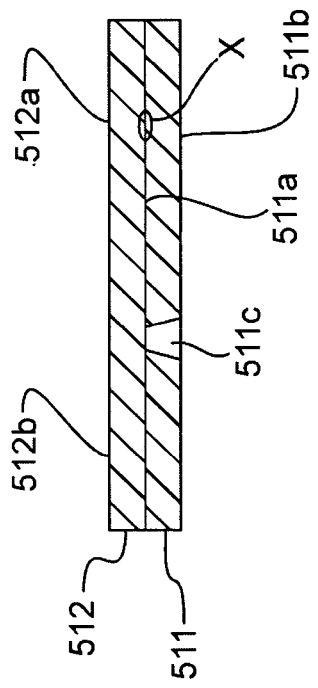
FIG. 54 is a cross-sectional view taken generally along the lines 54-54 of FIG. 53.
Figure 56:
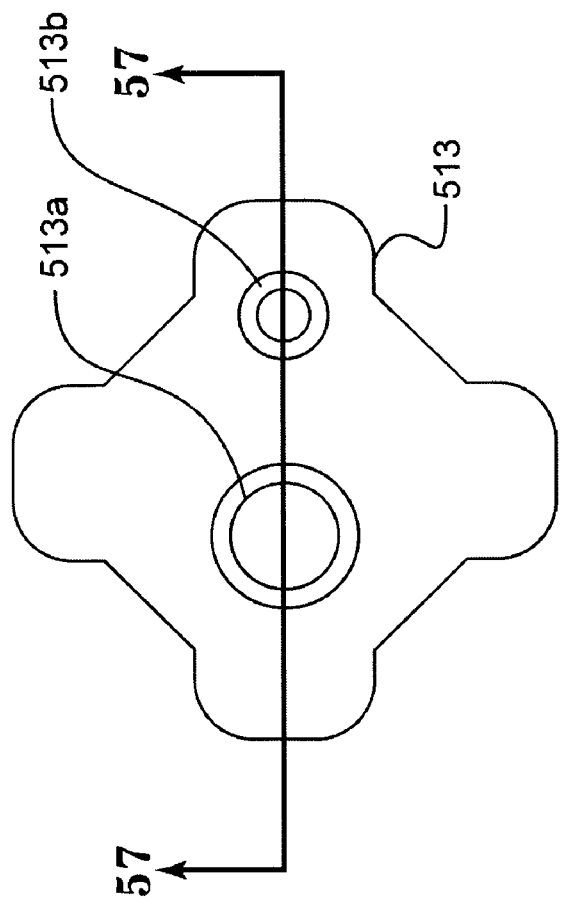
FIG. 56 is a top plan view of a gasket shown in FIG. 50.
Figure 57:
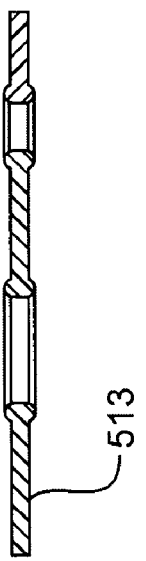
FIG. 57 is a cross-sectional view taken generally along the lines 57-57 in FIG. 56.

The flow restrictor 510 is shown more clearly in FIG. 52 and some of its components in FIGS. 53-57. The flow restrictor 510 is a chip assembly that includes a first substrate 511 and a second substrate 512. The term chip assembly is used as it is formed in a similar fashion as that of forming a micro chip. The substrates 511 and 512 are preferably glass or silicone. The substrate 511 is generally square and has a first planar surface 511a and a second planar surface 511b. The second substrate 512 has a first planar surface 512a and a second planar surface 512bThe planar surfaces 511a and 512a are positioned proximate each other. The substrate 511 has a first opening 511c that extends from the first surface 511a to the second surface 511b. Similarly a second opening 511d also extends from the surface 511a to the surface 511b. A continuous channel 512c is micro-machined on the surface 512a. The path of the channel 512c is best shown in FIG. 53 and the shape of the channel 512c is best shown in FIG. 55. The channel 512c is 0.02 mm ±200 nm in width and a height of 0.005 mm±50 nm. The channel 512c is spaced approximately 0.1 mm from the adjacent channel. The amount of drugs that flow thru can be varied by varying the size and length of the channel. The channel 512c provides for a flow path for the drugs. The holes 511c and 511d are powder blasted. The channels 512c are formed by micro-machining. Such a micro-machining process is common in the semiconductor industry as well as in the micro-fluidic industry. The opening 511c is proximate the outlet of the drug storage chamber 506 and the opening 511d is proximate the catheter exit 530. A catheter 531 is operatively connected and is in fluid communication with the exit 530. Two gaskets 513 and 514 are positioned around the substrates 511 and 512. The gasket 513 has two openings 513a and 513b which are over the openings 511c and 511d. The gasket 514 is shown as having similar holes. However, the holes are not necessary and are shown only because the gaskets 513 and 514 are the same so that it is not necessary to have an additional part. However, it is understood that the holes are not necessary in gasket 514. A shim 515 is positioned on top of the gasket 514. The flow restrictor is compressed together by screws 519 that are secured in bosses 520 that have threads to accept the screws 519. As previously discussed, FIG. 50 shows an embodiment that is useful for a prototype design. For a production model the screws 519 could be eliminated and the flow restrictor formed with a compression fit and simply placed in the inner wall 502.

The diaphragms 105, 205, and 505 all move from a full position, where the diaphragm is down, as viewed in the Figures to an empty position. This provides for a larger drug storage subchamber. Then, as the drug is dispensed, the diaphragms "move over center". That is, the centers, along with the whole diaphragm, move up until the diaphragms are proximate the underneath portion of the top half 101a, 201a, and 501a. This provides for a good volume efficiency as at least 90% of the drug in the drug storage subchamber is able to be dispensed.

The present invention, because of its small size, is able to be used in a number of locations in the body. The pumps may be placed in nearly any location in the body including the cranium, behind the ear or the pectoral region. It is intended to be implanted in close proximity to the desired delivery site.

In addition to the foregoing design concepts, other concepts that could also be utilized include glass tubing similar to that used in the ISOMED® pump sold by Medtronic, Inc., by utilizing smaller tube diameters. A micro-thread groove could also be cut on a cylinder surface and then enclosed by similar smooth surface installed as an interference fit such as a heat press. A compressed elastomer could cover machined titanium channels. Metal injection molding could be used. A water jet guided laser cutting of a groove in titanium or other metals is another possibility. Precision machining of grooves in titanium or other metals, chemical etching of grooves in titanium or other metals and micro-laser sintering may also be incorporated.

The invention is a pump mechanism for use in an implantable drug delivery system. The pump has a pump diaphragm that divides a chamber into a drug storage subchamber and a propellant subchamber. The propellant subchamber is adapted and configured to receive a suitable propellant. The diaphragm is constructed from a superelastic metal material. One example of such a material is NITINOL, a superelastic Ni—Ti alloy. In a preferred embodiment the diaphragm has a configuration that allows the diaphragm to go over center and have a relatively large deflection with minimal stress. One such example of a configuration is a dome. It is understood that the infusion device may be either a fixed rate or a variable rate pump. The overall size of the pump is 30 cc or less and preferably is approximately 4 cc in size. The smaller 4 cc size pump would have drug storage subchamber of approximately 1 ml.

The infusion device is preferably refillable and includes a fill port in fluid communication with the drug storage subchamber. A septum is positioned in the fill port. Further, a filter is positioned between the drug storage subchamber and a flow restrictor, which is in turn in fluid communication with the outlet. The septum may be a silicone septum and the filter a titanium filter.

The infusion device mechanism may include a suitable flow restrictor positioned between the drug storage subchamber and the outlet. Examples of the flow restrictor would include a micro-machined glass or silicone chip assembly, a glass capillary tube; micro-threads around the housing; a plurality of multi-outlet discs or a silicone sealing over grooves. Again, the pumps and devices thus far described may also be used as non-implantable pumps.

Thus, embodiments of the MINIATURE PUMP FOR DRUG DELIVERY are disclosed.

One skilled in the art will appreciate that the present invention can be practiced with embodiments other than those disclosed. The disclosed embodiments are presented for purposes of illustration and not limitation.

We claim:

1. An infusion device for use in delivering drugs, the device comprising:
    a) a housing having a chamber, the housing having an outlet;
    b) a diaphragm operatively connected to the housing, the diaphragm dividing the chamber into a drug storage subchamber and a propellant subchamber, the diaphragm constructed from a shape memory alloy material, the diaphragm is configured to go over center for greater volume efficiencies;
    c) the propellant subchamber adapted and configured to receive a suitable propellant;
    d) the shape memory alloy selected for low bending stresses, wherein significant pressure changes are not imparted to the drug storage subchamber; and
    e) the drug storage subchamber adapted and configured to receive a suitable drug, the drug storage subchamber having an outlet in fluid communication with the outlet of the housing.

2. The infusion device of claim 1, further comprising a septum operatively connected to the housing and in fluid communication with the drug storage subchamber.

3. The infusion device of claim 1, wherein the diaphragm is constructed from a Ni—Ti alloy.

4. The infusion device of claim 1, further comprising a flow restrictor having a first end in fluid communication with the outlet of the drug storage subchamber and a second end in fluid communication with the housing outlet.

5. The infusion device of claim 4, the flow restrictor being a micro-machined flow resistor.

6. The infusion device of claim 5, the micro-machined flow resistor comprising:
    a) a first substrate member having a planar top surface;
    b) a second substrate member having a planar bottom surface, the bottom surface of the second substrate member positioned on the top surface of the first substrate member to form a chip assembly;
    c) one of the top surface and bottom surface having a channel machined thereon; and
    d) the chip assembly having an inlet in fluid communication with the drug storage subchamber outlet and an outlet in fluid communication with the housing outlet.

7. The infusion device of claim 6, wherein the first and second substrates are glass substrates.

8. The infusion device of claim 6, wherein the channel is sized for a flow rate of approximately 1 ml per month.

9. The infusion device of claim 6, wherein the channel is 0.02 mm in width±200 nm and a depth of 0.005 mm±50 nm.

10. The infusion device of claim 5, wherein the pump is a fixed rate pump.

11. The infusion device of claim 1, wherein the drug reservoir, when fully dispensed, dispenses at least 90% of the drug reservoir, when full.

12. The infusion device of claim 1, wherein the shape memory alloy is a Ni—Ti alloy.

13. The infusion device of claim 12, wherein the Ni—Ti alloy is superelastic.

14. The infusion device of claim 12, wherein the Ni—Ti alloy is superdeformable.

15. The infusion device of claim 1, wherein the infusion device is an implantable infusion device.

16. An infusion device for use in delivering drugs, the device comprising:)
    a housing having a chamber, the housing having an outlet;
    b) a diaphragm operatively connected to the housing, the diaphragm dividing the chamber into a drug storage subchamber and a propellant subchamber, the diaphragm constructed from a shape memory alloy, the diaphragm is configured to go over center for greater volume efficiencies;
    c) the propellant subchamber adapted and configured to receive a suitable propellant;
    d) the shape memory alloy selected for low bending stresses, wherein significant pressure changes are not imparted to the drug storage subchamber;
    e) the drug storage subchamber adapted and configured to receive a suitable drug, the drug storage subchamber having an outlet in fluid communication with the outlet of the housing; and
    f) a flow restrictor having a first end in fluid communication with the outlet of the drug storage subchamber and a second end in fluid communication with the housing outlet, the flow restrictor being a micro-machined flow restrictor, the flow restrictor comprising:
        i) a first glass member having a planar top surface;
        ii) a second glass member having a planar bottom surface, the bottom surface of the second glass member positioned on the top surface of the first glass member to form a chip assembly;
        iii) one of the top surface and bottom surface having a channel machined thereon; and
        iv) the chip assembly having an inlet in fluid communication with the drug storage subchamber outlet and an outlet in fluid communication with the housing outlet.

17. The infusion device of claim 16, wherein the shape memory alloy is a Ni—Ti alloy.

18. The infusion device of claim 16, wherein the infusion device is implantable.

19. The infusion device of claim 3, wherein the Ni—Ti alloy is in an Austenitic phase wherein the Ni—Ti alloy provides for superelastic properties to accommodate bending.

20. The infusion device of claim 3, wherein the Ni—Ti alloy is in a Martensitic phase wherein the Ni—Ti alloy provides for superelastic properties to provide for an ability to undergo large strains and deformation without fracture.

21. The infusion device of claim 17, wherein the Ni—Ti alloy is in an Austenitic phase wherein the Ni—Ti alloy provides for superelastic properties to accommodate bending.

22. The infusion device of claim 17, wherein the Ni—Ti alloy is in a Martensitic phase wherein the Ni—Ti alloy provides for superdeformable properties to provide for an ability to undergo large strains and defoiiiiation without fracture.

* * * * *

UNITED STATES PATENT AND TRADEMARK OFFICE
CERTIFICATE OF CORRECTION

| | | Page 1 of 1 |
|---|---|---|
| PATENT NO. | : 7,931,643 B2 | |
| APPLICATION NO. | : 11/490876 | |
| DATED | : April 26, 2011 | |
| INVENTOR(S) | : Olsen et al. | |

It is certified that error appears in the above-identified patent and that said Letters Patent is hereby corrected as shown below:

Col. 10, Line 13: "comprising: ) a housing" should read --comprising: a) a housing--

Col. 10, Line 64: "and defoiiiiation" should read --and deformation--

Signed and Sealed this
Fourth Day of October, 2011

David J. Kappos
*Director of the United States Patent and Trademark Office*